Figure 1:
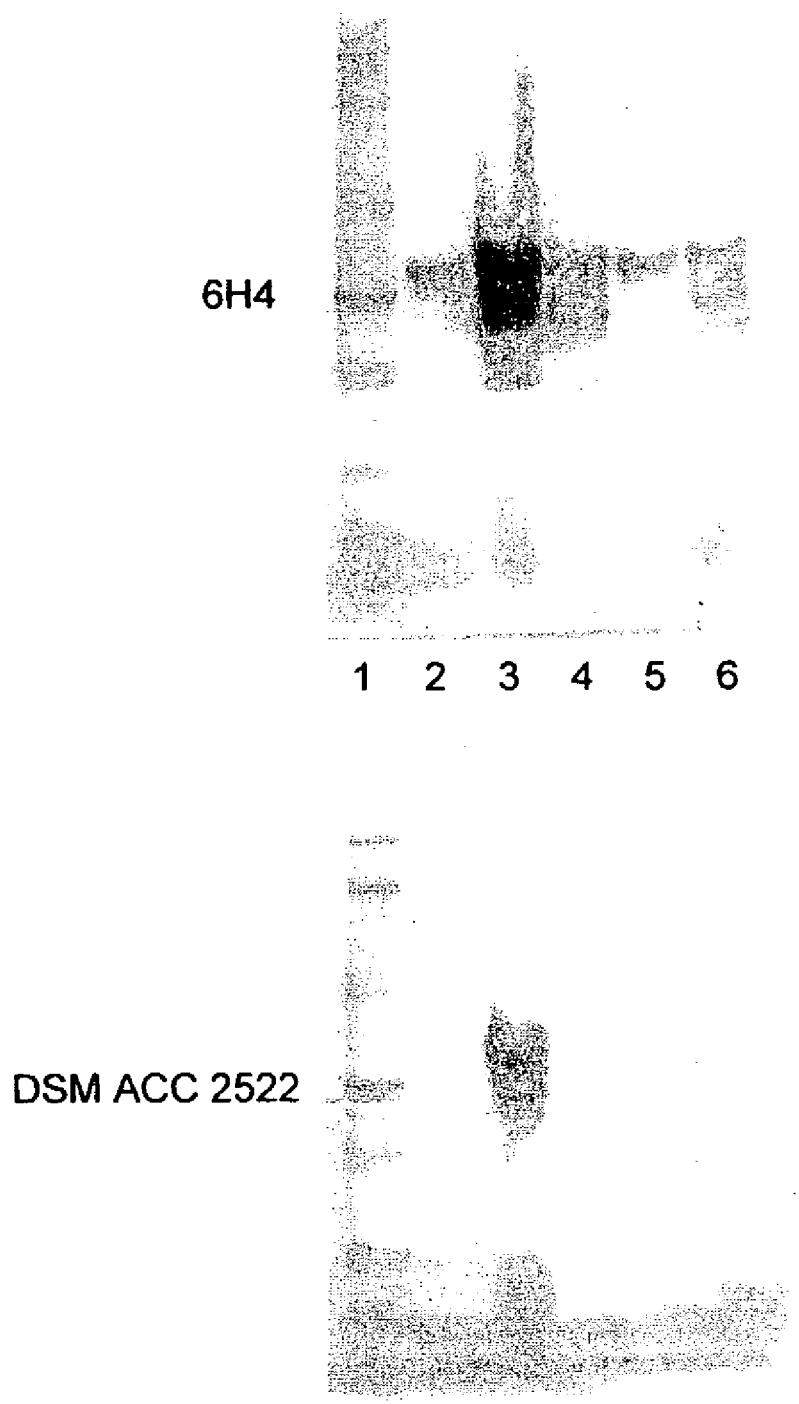

US007202021B2

(12) United States Patent
Vey et al.

(10) Patent No.: US 7,202,021 B2
(45) Date of Patent: Apr. 10, 2007

(54) ANTIBODIES FOR SPECIFICALLY DETECTING PATHOGENIC PRIONS OF HUMAN ORIGIN, AND DETECTION METHODS CARRIED OUT USING THESE ANTIBODIES

(75) Inventors: Martin Vey, Marburg (DE); Weigand Lang, Coelbe (DE); Albrecht Groener, Marburg (DE); Anne Bellon, Marburg (DE)

(73) Assignee: Aventis Behring GmbH, Marburg (DE)

( * ) Notice: Subject to any disclaimer, the term of this patent is extended or adjusted under 35 U.S.C. 154(b) by 611 days.

(21) Appl. No.: 10/273,282

(22) Filed: Oct. 18, 2002

(65) Prior Publication Data

US 2003/0092094 A1 May 15, 2003

(30) Foreign Application Priority Data

Oct. 19, 2001 (DE) ................................ 101 52 677

(51) Int. Cl.
*C12N 5/12* (2006.01)
*C12Q 1/70* (2006.01)
*C07K 16/00* (2006.01)
*C07H 21/04* (2006.01)
*C12N 15/63* (2006.01)

(52) U.S. Cl. ...................... 435/5; 530/388.15; 435/326

(58) Field of Classification Search ............ 530/388.1, 530/389.1, 350

See application file for complete search history.

(56) References Cited

U.S. PATENT DOCUMENTS

| | | | |
|---|---|---|---|
| 4,806,627 | A | 2/1989 | Wisniewski et al. |
| 6,077,938 | A | 6/2000 | Dickson et al. |

FOREIGN PATENT DOCUMENTS

| | | | |
|---|---|---|---|
| EP | 0 886 141 A1 | 12/1998 | |
| EP | 1 229 331 A1 | 8/2002 | |
| JP | 2000-060551 | 2/2000 | |
| WO | WO 97/37411 | 10/1997 | |
| WO | WO 98/37411 | 8/1998 | |
| WO | WO 00/48003 | 8/2000 | |
| WO | WO 01/68695 | 9/2001 | |
| WO | WO 02/086168 | 10/2002 | |

OTHER PUBLICATIONS

Wopner et al. Analysis of 27 mammalian and 9 avian PrPs reveals high conservation of flexible regions of the prion protein. Journal of Molecular Biology (1999) vol. 289, pp. 1163-1178.*
Groschup et al. Antigenic features of prion proteins of sheep and of other mammalian species. Journal of Immunological Methods (1997) vol. 207, pp. 89-101.*
Khalili-Shirazi et al., Protein conformation significantly influences immune response to prion protein. Journal of Immunology (2005) vol. 174, pp. 3256-3263.*
Burgess et al., Possible dissociation of the heparin-binding and mitogenic activities of heparin binding growth factor-1 from its receptor-binding activities by site directed mutagenesis of a single lysine residue. Journal of Cell Biology (1990) vol. 111.*
Tao et al., Studies of aglycosylated chimeric mouse-human IgG. The Journal of Immunology (1989) vol. 143 No. 8, pp. 2595-2601.*

Lazar et al. Transforming growth factor alpha; mutations of aspartic acid 47 and leucine 48 results in different biological activities. Molecular and Cellular Biology (1988) vol. 8, No. 3, pp. 1247-1252.*

Zhu B.T., Human and animal spongiform encephalopathies are the result of chronic autoimmune attack in the CNS: a novel medical theory supported by overwhelming experimental evidence. Histology and Histopathology (2005) vol. 20, pp. 575-592.*

Korth, C., et al., "Prion ($PrP^{Sc}$)-specific epitope defined by a monoclonal antibody", *Nature* 390:74-77, Nov. 16, 1997.

Krasemann, S., et al., "Induction of antibodies against human prion proteins (PrP) by DNA-mediated immunization of $PrP^{0/0}$ mice", *J. Immunological Methods* 199:109-118, 1996.

MacGregor, I., "Prion protein and developments in its detection", *Transfusion Medicine*, 11:3-14, 2001.

Muramoto, T., et al., "Analysis of Gerstmann-Straussler syndrome with 102Leu219Lys using monoclonal antibodies that specifically detect human prion protein with 219Glu", *Neuroscience Letters* 288:179-182, 2000.

European Patent Office Search Report; EP 02 02 2825; issued Oct. 8, 2003.

European Search Report Dated Nov. 28, 2003.

Brodnicki, T. et al., Mar. 1996, and Epitope Mapping of Single-chain T Cell Receptors with Monoclonal Antibodies, Molecular Immunology, 33(3): 253-263.

Helfrich, W. et al., 1994, "Epitope Mapping of SCLC-cluster-2 MAbs and Generation of Antibodies Directed Against New EGP-2 Epitopes," International Journal of Cancer Supplement, 8:64-69 (abstract only, from Database Medline 'Online!).

(Continued)

*Primary Examiner*—Bruce R. Campell
*Assistant Examiner*—Michelle Horning
(74) *Attorney, Agent, or Firm*—Finnegan, Henderson, Farabow, Garrett & Dunner, L.L.P.

(57) ABSTRACT

This application includes description of antibodies for specifically detecting prions of human origin and methods for detecting pathogenic prions. In some embodiments, the antibodies bind to an epitope characteristic for a human prion protein which is not found in the prion proteins of other species. In some embodiments, the antibodies are not cross-reactive with cow, Syrian Gold hamster, mouse, or rat prions. The application also includes a conformation-dependent immunoassay method for detecting pathogenic prions in a sample containing a prion (PrP) protein. The PrP protein may be present in a first conformation and a second conformation, such as $PrP^{C}$ and $PrP^{Sc}$ in which the two conformations have different binding affinity for the antibody used to detect them.

11 Claims, 3 Drawing Sheets

OTHER PUBLICATIONS

Liao, J. et al., 1993, "Monoclonal Antibodies Against Brain Acetylcholinesterases which Recognize the Subunits Bearing the Hydrophobic Anchor," European Journal of Biochemistry, 215(2): 333-340 (abstract only, from Database Biosis 'Online!').

McRae, J. et al., Mar. 2, 2001, "Human Factor H-related Protein 5 (FHR-5): A new complement-associated protein," J. of Biological Chemistry, 276(9): 6747-6754.

Ryu, C. J. et al., 1996, "A Humanized Antibody with Specificity for Hepatitis B Surface Antigen," Human Antibodies and Hybridomas, 7(3): 113-122 (abstract only, from Database Biosis 'Online!').

European Search Report Dated Jan. 12, 2004 (in German).

Bolton, D.C., et al., "Isolation and Structural Studies of the Intact Scrapie Agent Protein", *Archives of Biochemistry and Biophysics*, 258 (2):579-590, Nov. 1, 1987.

Prusiner, S.B., "Prions", *Proc. Natl. Acad. Sci. USA*, 95:13363-13383, Nov. 1998.

Prusiner, S.B., et al., "Purification and Structural Studies of a Major Scrapie Prion Protein", *Cell*, 38:127-134, Aug. 1984.

Prusiner, S.B., et al., "Further Purification and Characterization of Scrapie Prions", *Biochemistry*, 21:6942-6950, 1982.

Prusiner, S.B., et al., "Concise Communications: Monoclonal Antibodies to the Cellular and Scrapie Prion Proteins", *The Journal of Infectious Diseases*, 154 (3):518-521, Sep. 1986.

Zanusso, G., et al., "Prion protein expression in different species: Analysis with a panel of new mAbs", *Proc. Natl. Acad. Sci. USA*, 95:8812-8816, Jul. 1998.

Harmeyer, S., et al., "Synthetic peptide vaccines yield monoclonal antibodies to cellular and pathological prion proteins of ruminants", *Journal of General Virology*, 79:937-945, 1998.

Krasemann, S., et al., "Generation of monoclonal antibodies against prion proteins with an unconventional nucleic acid-based immunication strategy", *Journal of Biotechnology*, 73:119-129, 1999.

Smales, M.C., "Protein Modification During Anti-Viral Heat-Treatment Bioprocessing of Factor VIII Concentrates, Factor IX Concentrates, and Model Proteins in the Presence of Sucrose", *Biotechnology and Bioengineering*, 77(1):37-48, Jan. 5, 2002.

\* cited by examiner

ANTIBODIES FOR SPECIFICALLY DETECTING PATHOGENIC PRIONS OF HUMAN ORIGIN, AND DETECTION METHODS CARRIED OUT USING THESE ANTIBODIES

This application claims priority to German Patent Application No. 101 52 677.6, filed Oct. 19, 2001.

The invention relates to antibodies which bind specifically to prions of human origin and to a method for detecting pathogenic prions, in particular causative agents of spongiform encephalopathy.

Prion diseases, such as Creutzfeldt-Jakob disease (CJD), can either develop as a result of inherited genetic defects or be acquired by routes of infection which are not yet fully understood. In addition, they also occur as spontaneous, so-called sporadic forms, for which a somatic mutation in the gene for the prion protein is postulated to be responsible (Prusiner, Proc. Natl. Acad. Scie U.S.A., 95, 13363–13383 (1998)). Iatrogenic routes of infection arise, for example, as a result of treatment with prion-contaminated growth hormones or sex hormones or corneal and meningeal transplants. The use of surgical instruments which are not adequately sterilized also constitutes a possible source of infection.

The prion proteins (abbreviated PrPs), which are 33 to 35 kD in size, occur in a natural physiological isoform ($PrP^c$) and in a pathologically infectious isoform ($PrP^{Sc}$), with the infectious isoform arising from the noninfectious physiological form as a result of a refolding of the secondary and tertiary structure. $PrP^{Sc}$ is most probably the only physical component of prions which is responsible for the transmission and pathogenesis of the prion diseases (Prusiner, Proc. Natl. Acad. Sci. U.S.A., 95, 13363–13383 (1998)).

It has already been disclosed by Prusiner et al., Cell 38, 127 (1984) and Biochemistry 21, 6942 (1982) that prion proteins are accessible to partial proteolysis. Since then, it has been found that, while $PrP^c$ is almost completely accessible to proteolysis, $PrP^{Sc}$ can only be degraded down to a size of 27 to 30 kD. This protein fragment, which is not accessible to further proteolysis, is termed a protease-resistant core, i.e. $PrP^{27-30}$ for short. It arises as the result of the degradation of approx. 67 amino acids at the $NH_2$ terminus and consequently consists of approx. 141 amino acids.

Methods for detecting the pathological prion isoforms have also already been described. Thus, for example, Barry and Prusiner J. Infect. Dis. 154, 518–521 (1986) describe a Western blot test which uses an anti-prion protein monoclonal antibody (MAB) 13A5. This MAB, which is specific for hamster PrP, was obtained from mice which had been immunized with purified, denatured $PrP^{27-30}$ which had been isolated from scrapie-infected hamsters.

Other antibodies, which similar to MAB 13A5 are directed against both $PrP^c$ and against $PrP^{Sc}$, provided this latter is present in denatured form, have also already been described (U.S. Pat. No. 4,806,627). Furthermore, immunizations have been carried out using recombinant prion proteins which had been expressed in bacteria, as described in Zanusso et al., Proc. Natl. Acad. Sci. USA, 95, 8812–8816 (1998). In addition, success has been achieved in preparing monoclonal antibodies by means of peptide immunization, as described in Harmeyer et al., J. Gen. Virology, 79, 937–945 (1998), and by means of nucleic acid immunization, as explained in Krasemann et al., J. Biotechnology, 73, 119–129 (1999).

Another application of these antibodies in addition to Western blotting, i.e. what is termed an ELISA (enzyme-linked immunosorbent assay), was mentioned in the Wisniewski et al. U.S. Pat. No. 4,806,627. In this ELISA, prions which had been fixed on a microtiter plate were bound by the MAB 3F4, and this latter antibody was then detected using a secondary antibody which catalyzed a dye reaction by way of an enzyme which was coupled to it.

In all these detection methods, the sample is pretreated with the enzyme proteinase K in order to remove any normal prion protein which is present in the sample and, consequently, to ensure that it is only the protease-resistant, pathogenic prion protein which is detected since the antibodies are of course also able to bind the normal prion protein with a high degree of affinity.

However, because of the labor intensity and time intensity which is required, the previously described methods, involving separation by electrophoresis and immobilization on membranes, in particular nitrocellulose membranes, and subsequent determination using anti-PrP antiserum are not suitable as methods for routine testing. Therefore, because of the enormous threat to the population posed by a possible transmission of spongiform encephalopathies, there is a great need for a rapid method for detecting prions, for example in human and veterinary diagnostics, with this method being able to detect the pathological prion isoform qualitatively and quantitatively in samples of body fluids and tissue samples.

Finally, a detection method which can be used for detecting the pathogenic conformation of the prion protein in a sample has already been disclosed in international patent application WO 98/37411. In this method, the sample is divided into two portions and the first portion is bound to a solid support and then contacted with a labeled antibody. This antibody binds to the nonpathogenic form of the prion protein with a higher affinity than it does to the nondenatured, pathogenic form of the protein. The second portion of the sample is then subjected to a treatment which results in the conformation of the pathogenic prion protein being altered, thereby drastically increasing its accessibility and consequently its affinity for the labeled antibody. The second portion of the sample, which has been treated in this way, is then brought into contact with a second support and reacted with a labeled antibody. The quantities of the labeled antibody which are bound in the first portion and in the second portion are then measured and compared with each other. The difference between the two measurement results indicates whether the pathogenic form of the prion protein was present in the sample. This detection method is termed a conformation-dependent immunoassay (CDI). The sensitivity of the CDI can be increased if the sample is subjected to a pretreatment with a proteolytic enzyme, for example proteinase K or dispase. The treatment with proteases destroys $PrP^c$ and irrelevant proteins in the sample and the protease-resistant $PrP^{27-30}$ is left in the sample.

The examination of human blood plasma for the presence of the pathogenic prion protein requires very sensitive and specific detection systems which also allow automation of sample testing. The detection of prions is even more difficult because the physiological processes underlying the pathological effects of prions are not yet known. In addition, no diagnostic reagents are thus far available which differentiate directly between the pathological isoform $PrP^{Sc}$ and the normal isoform $PrP^c$, which is usually present in great excess and which cross-reacts with all the other antibodies which have been employed for detection of prions so far.

A common feature in all of the previously known methods for detecting pathogenic prion proteins is that it is not possible to distinguish unambiguously whether the pathogenic prion proteins detected are prion proteins of human origin or prion proteins which are derived from other species. The MAB 3F4, which is widely available and which is used for diagnosing human prion diseases, also reacts with the prion proteins of other mammal species, for example with the hamster prion protein. Such a differentiation would be very important for determining whether the pathogenic prion protein which been found in a human body derived from the exterior or whether the pathogenic prions have been initially formed in the human body. Animal prions could be transmitted to humans as a result of exposure in the workplace, for example in a laboratory or animal housing in which prions are being handled, on the one hand, and, on the other hand, also by the consumption of prion-contaminated foodstuffs or, possibly, even by the use of contaminated cosmetic or pharmaceutical products. Precise knowledge of the source of infection could make it possible to develop effective protective measures.

Highly specific methods for detecting pathogenic prions of human origin have been lackingthus far because of the fact that it has not been possible to use the previously known antibodies to selectively recognize an epitope which only occurs in prions of human origin and but is absent in prions of animal origin at the same time.

Surprisingly, it has now been found that it is possible to discover antibodies, in particular monoclonal antibodies, which recognize an epitope which is characteristic for a human prion protein but which do not react with a prion protein of animal origin. The selective recognition is preferably seen by using the western-blot technique. Examples of antibodies of this nature are the monoclonal antibodies which are formed by the hybridoma cell lines DSM ACC 2522, DSM ACC 2523 and DSM ACC 2524. These monoclonal antibodies do not exhibit any cross-reactivity with the PrP from the African Green monkey or with bovine, hamster, rat or mouse PrP, when separated in SDS-polyacrylamide-gels, transferred to nylon-membranes and detected with the antibodies.

Each of cell lines DSM ACC 2522, 2523, and 2524 are deposited at the DSMZ-Deutsche Sammlung von Mikroorganismen und Zellkulturen GmbH at Mascheroder Weg 1b, D-38124 Braunschweig, Germany. Each was deposited on Aug. 30, 2001.

Using these novel monoclonal antibodies, it has now been possible, for the first time, to develop methods for the highly specific, highly sensitive detection of prion proteins of human origin, for example an appropriate Western blotting method, as described above.

Figure 2A:
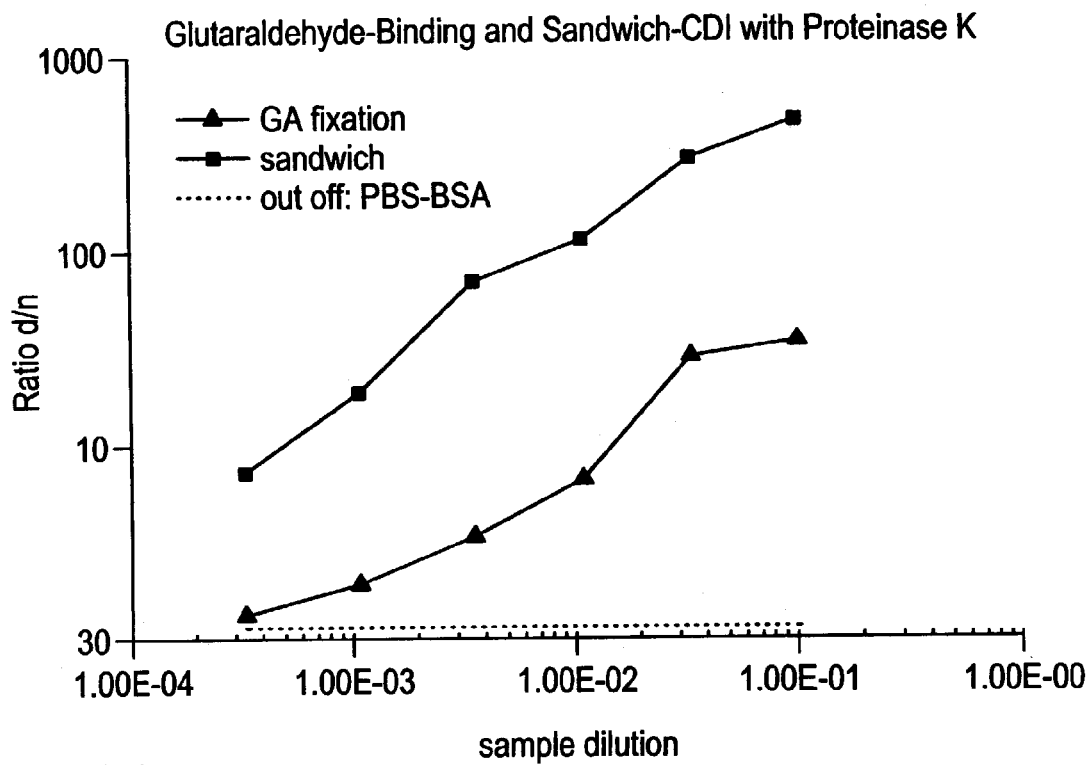
Figure 2B:
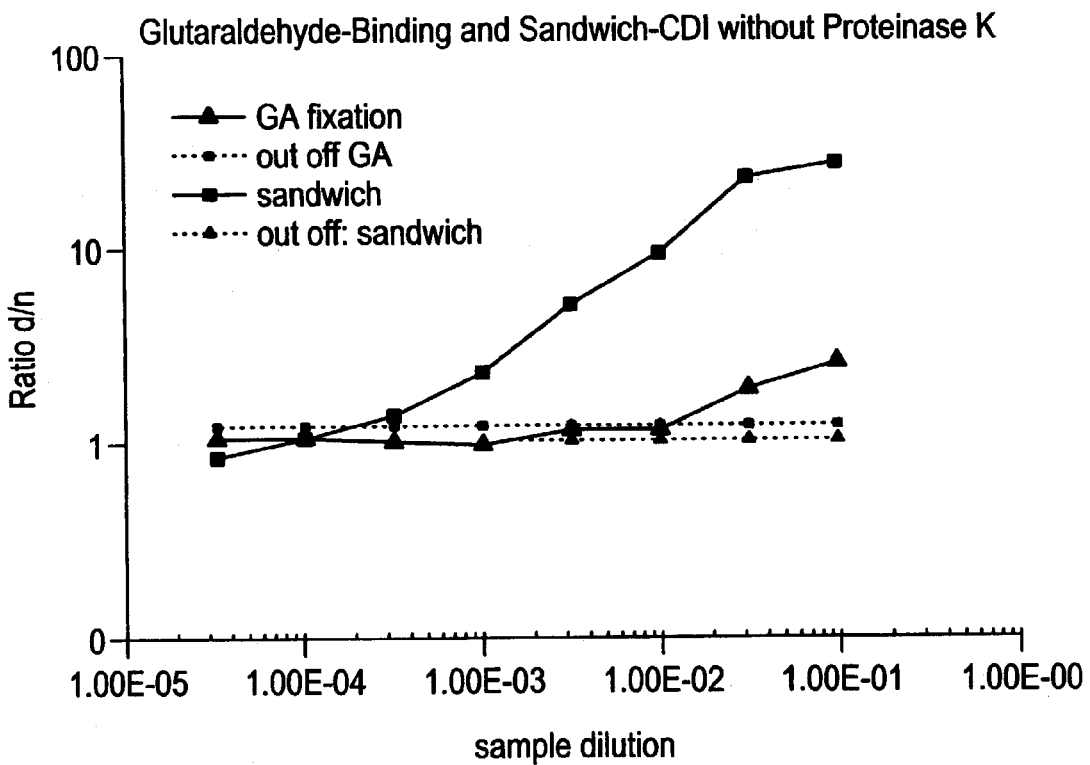

The conformation-dependent immunoassay method CDI for detecting pathogenic prion proteins in a sample of a body fluid or a liquefied sample of body-tissue is also of particular interest. The CDI which was previously used only involved fixing the sample to be investigated on a solid support by means of chemical crosslinking. As a result, the prion proteins contained in the sample were not selectively enriched from the sample; instead, they were attached to the support substance together with many other, irrelevant proteins. This denotes a loss of sensitivity, since many prion proteins in the sample are not even bound on the support material at all. This interfering effect becomes noticeable, in particular, in samples which have a high protein content, e.g. plasma. Furthermore, this interfering effect greatly restricts a further use of the CDI, namely determination of the prion content in samples without any pretreatment with proteinase, since omitting the proteinase treatment increases this interfering effect of the irrelevant proteins in the sample even further. The monoclonal, human PrP-specific antibodies which are produced by the deposited cell lines DSM ACC 2522, DSM ACC 2523 and DSM ACC 2524 abolish this interfering effect since they can be applied, for example, as capturing antibodies to the support material and then bind the human prion proteins which are present in the sample selectively on the support material. In this way, substantially more prion proteins in the sample are bound on the support material and, at the same time, the sensitivity of the test is increased 10–30-fold (Example 2, FIG. 2A). Consequently, any interfering effect due to irrelevant proteins is of no significance either, and a high degree of test sensitivity is achieved even when the samples are not pretreated with a protease (Example 2, FIG. 2B): in this context, the use of the capturing antibody even increases the test sensitivity from 100- to 300-fold when compared with the glutaraldehyde cross-linking method. For the purposes of simplification, this configuration, in which the capturing antibody is applied to the support, is termed a sandwich configuration (FIG. 2). The improved CDI detection method comprises the following steps:

a) adding one of the abovementioned monoclonal antibodies, which is bound to a solid support and which has a higher affinity for the normal, nonpathogenic conformation of the prion protein, to a first portion of the sample, and determining the concentration of the prion protein;

b) treating the second portion of the sample in order to increase the accessibility of the pathogenic conformation for the monoclonal antibody;

c) adding the monoclonal antibody to the second portion which has been treated in this way for the purpose of determining the second concentration;

d) comparing the first concentration with the second concentration for the purpose of detecting the presence of the pathogenic conformation of the prion protein.

Monoclonal antibodies which are formed by the hybridoma cell lines DSM ACC 2522, DSM ACC 2523 and DSM ACC 2524 are particularly suitable for this detection method. An important step in the immunoassay detection method consists of subjecting one part of the sample to be investigated to physical or chemical conditions which lead to a change in the conformation of the pathological form of the pathogenic prion protein, with the change in conformation leading to an increase in accessibility for the antibody. The change in conformation can be brought about by heat, pressure or the action of chemical substances. It is sufficient if at least 2% of the pathogenic prion protein which is present is converted into a conformation which is accessible for the monoclonal antibody.

Suitable support materials for immobilisation of the prion proteins are chromatography resins, agarose, microtiter plates, nitrocellulose membranes, nylon membranes or magnetic beads which are customarily employed. The prion proteins which are bound to these support materials are detected, for example, using an ELISA method in which a second, labeled antibody is brought into contact with the immobilised prion proteins. The monoclonal antibody 3F4 has proved to be suitable for use as the second, labeled monoclonal antibody. It can be labeled with a radioactive group, an enzyme or a fluorescent group.

The advantage of the immunoassay detection method according to the invention is that the sensitivity of the prion protein detection is increased about 10- to 300-fold compared to the sensitivity of known conformation-dependent immunoassays which are disclosed, for example, in the international patent application WO 98/37411. This is achieved by using the monoclonal antibodies according to the invention, which make it possible to selectively enrich the prion proteins from the sample to be investigated.

It was possible to demonstrate the reliability and sensitivity of the detection method according to the invention by adding quite small quantities of prions to groups of 10 and 100 plasma samples and then using the immunoassay according to the invention to detect the prions with confidence in every case. This conformation-dependent immunoassay detects prions causing the commone forms of Creutzfeldt-Jakob disease (CJD) as well as prions of the new variant form of CJD (vCJD), which is characterized, inter alia, by the appearance of prions in the lymphatic organs of patients. By contrast, no positive reaction at all, apart from minute backgroundsignals, was found in any of the plasma samples to which no prions were added. It was possible to achieve such results both by using highly purified prion proteins and by using homogenized brain samples derived from infected animals. Even when the pretreatment with a protease, which is required in all the previous methods, is not carried out, the immunoassay method according to the invention can still be used to establish the presence of prion proteins with a high degree of confidence.

A special feature of the monoclonal antibodies according to the invention is that they only recognize human prion proteins. This is probably due to the fact that they recognize a very specific amino acid sequence in the human prion protein, which sequence is not present in other mammals.

This results in the immunoassay according to the invention having novel applications. Thus, if a pathological prion protein is found in the human body when using the antibodies according to the invention, it is then definite that this PrP$^{Sc}$ was initially formed in the human body. If, on the other hand, no signal is found when these antibodies according to the invention are used, but a signal is found when the previously known antibodies, e.g. the onesupplied by the company Prionics, which is called the 6H4 antibody, are used, this pathological prion protein must then be of animal origin. In this case, therefore, the person being investigated has become infected by inoculation with prions of animal origin. In this way, prion proteins of unknown origin can be assigned to an animal or human source and the propagation routes of pathological prions thereby elucidated.

The binding sites, i.e. epitopes, for the monoclonal antibodies according to the invention were also characterized. The epitope for the monoclonal antibodies DSM ACC 2522, DSM ACC 2523 and DSM ACC 2524 is determined crucially by the single disulfide bridge in the prion protein. Accordingly, the disulfide bridge is either itself a part of the epitope and interacts with the antigen-binding site of the monoclonal antibody, or the disulfide bridge links together protein regions which are otherwise at a distance from each other and which now, due to the sulfur bridge, form a composite, conformational epitope which is only present in the prion protein under oxidizing conditions. This is made clear in Example 4 and FIG. 3.

The antigenicity of proteins may be characterized by their respective binding to antibodies, both poly- and monoclonal-antibodies, to single-chain antibodies or in phage-display systems. Antibodies bind to a specific amino-acid structure of the target-protein, the epitope. The characterization of such properties can be accomplished by techniques which are known to the one skilled in the art per se, techniques such as Western-Blot, binding of antibodies to peptides, which have been synthesized as overlapping partial sequences of the target-protein. sequence (or nucleic acid sequence respectively), ELISAs with immobilized target-protein, binding of the antigen/antibody-complex to Protein A or immunoprecipitation. In general epitopes may be continuous (linear) or discontinuous (conformational), thus different methods may be used respectively. Linear epitopes consist of a continuous sequence of amino acids in a protein molecule, the spatial arrangement of the protein (secondary, tertiary or quarternary structure) have no impact on the epitope and the binding of antibodies to this epitope. Thus, the denaturation of the protein, for instance by SDS or chaotropic agents, has no impact on the epitope and the binding of antibodies to this epitope. These epitope may be characterized by their binding to overlapping partial-sequences of the target-protein in an ELISA. If an antibody binds to the target-protein as determined in an ELISA, in a dot-blot assay or by immunoprecipitation, without prior denaturation and not after denaturation, then the epitope is discontinuous (or conformational), i.e. the amino-acids comprising the epitope are present on the protein not in a linear sequence but are on separate parts regions of the protein and spatially aligned because of the three-dimensional arrangement of the protein. This arrangement of the amino acids comprising a conformational epitope may be spanning different molecules or remote domains of the same protein.

Surprisingly it was found during the characterization of the binding characteristics of the monoclonal antibodies secreted by hybridomas DSM ACC 2522, DSM ACC 2523 and DSM ACC 2524 that the denatured protein reacts with the antibodies in the Western-Blot (indication for a linear epitope), but not with overlapping peptides (indication for a conformational epitope). The analysis of the amino acid sequence of the potential antibody binding site revealed that a disulfide bridge was in this area. We analyzed whether the disulfide-bridge led to the existence of a conformational (discontinuous) epitope.

Disulfide-bridges are not destroyed by conventional protein-denaturing conditions, thus in the Western-Blot (after separation of the proteins by their apparent size in SDS-PAGE and subsequent transfer to a membrane) the protein will be incubated with an aqueous solution containing primary antibody, followed by the detection with labeled secondary antibodies which are directed against the primary antibody. If the disulfide bridge is destroyed by reduction, the epitope will be destroyed, too, and the antibody can not bind any longer. The use of overlapping peptides, which the one skilled in the art uses to identify linear epitopes, which can be detected with the Western-Blot technique, did not yield a result in the characterization of the epitopes of the antibodies secreted by hybridomas DSM ACC 2522, DSM ACC 2523 and DSM ACC 2524. This is because the disulfide-bridge could not be expressed in the peptides.

The correct development of disulfide-bridges is an important step during the maturation of proteins. In many cases disulfide-bridges are of utmost importance for the stability and function of proteins. Before the instant invention was made it was not possible to detect and. characterize the correct development of such disulfide-bridges.

This surprising finding, i.e. the detection of disulfide bridge based epitopes, can be used for the characterization of proteins, by producing antibodies or other high-affinity ligands against proteins containing disulfide-bridges (under oxidizing conditions). The one skilled in the art knows how to select the appropriate ligands by determining the binding to the protein with disulfide-bridges (oxidizing conditions) and without (reducing, conditions). To elicit such antibodies, one can immunize animals with proteins containing such disulfide-bridges. The proteins may be produced recombinantly, for instance in bacteria-, yeast-, plant-, insect- or mammalian cells or may be expressed in-vitro and may be isolated by conventional isolation techniques, known to the one skilled in the art. The proteins may also be isolated from tissue, organs, liquids, mixtures or other sources without over-expression. The proteins may be utilized for the immunization in a reduced or oxidized state. Other high affinity ligands, such as single-chain antibodies or peptide-ligands, may be identified in so-called "Phage-Display-Libraries", by using for the screening the target-protein in reduced and oxidized form, respectively.

An antibody produced in such a way, could be used to easily analyze the correct state of proteins which has been treated in a certain way (SMALES, 2002) or which has been expressed recombinantly in foreign organism.

The implementation of the detection method according to the invention is illustrated by the following examples:

EXAMPLES

1. Use of the Monoclonal Antibody Derived from the Hybridoma Cell Lines DSM ACC 2522, DSM ACC 2523 and DSM ACC 2524 to Detect $PrP^c$ from Various Species by Western Blotting In order to detect $PrP^c$ from different species, equal amounts (weight) of brain from an African Green monkey, a cow, a Syrian Gold hamster, a rat and a transgenic mouse expressing human PrP were homogenized in a phosphate-buffered saline solution (PBS) using an Ultra Turrax tissue grinder, and a final concentration of 10% (weight/volume) was established. Large tissue fragments were removed by centrifuging for 15 minutes at 500×g and room temperature. Equal volumes of PBS containing 4% sarcosyl were added to the supernatant. For separation of proteins, these lysates were mixed with the the SDS sample buffer for gel electrophoresis and boiled at 100° C. for 10 minutes. 20 µl of the brain lysate of each species were then loaded onto a 10% SDS polyacrylamide gel (Novex) and the proteins were separated by electrophoresis at 150 volts over a period of 45 minutes. The proteins were then transferred to nylon membranes (millipores) by means of electrotransfer. The membranes were then blocked at room temperature for 60 minutes with TBST (tris-buffered saline/0.1% Tween 20 (Sigma)) containing 1% bovine serum albumin (BSA, Merck) and then incubated, at room temperature, for one hour while shaking, either with the monoclonal antibody 6H4 (obtainable from Prionics, Switzerland) which was diluted 1:5000 in TBST, or with the monoclonal antibody from the hybridoma cell line DSM ACC 2522, DSM ACC 2523 or DSM ACC 2524, which was diluted 1:1 000 in TBST, or with TBST. After having been washed three times with TBST, the membranes were incubated with a goat anti-mouse IgG antibody conjugated with alkaline phosphatse (Amersham) diluted 1:5 000 in TBST for one hour at room temperature while shaking. After having been washed five times with TBST, the membranes were incubated with the detection reagent (Amersham).

Brain proteins from various species were blotted onto nylon membranes and incubated with PrP-specific monoclonal antibodies, with the following results being observed:

While the monoclonal antibodies obtained from the cell lines DSM ACC 2522, DSM ACC 2523 and DSM ACC 2524 do not possess crossreactivity with bovine, hamster or rat PrP, or with the PrP from the African Green monkey, they bind unambiguously to human prion protein.

2. Improved, Conformation-dependent Immunoassay Method Using the Monoclonal Antibody from the Hybridoma Cell Lines DSM ACC 2522, DSM ACC 2523 and DSM ACC 2524 as the Binding Reagent: Sandwich

CDI

The brain of a transgenic mouse which was expressing human $PrP^c$ and was infected with the sporadic form of Creutzfeldt-Jakob disease (sCJD) was isolated from a euthanized mouse at the first sign of prion disease, i.e. about 150 days after intracerebral infection with brain homogenate from a patient who had died of CJD. The brain was lyzed using the methods for lysate preparation described in Example 1. The brain lysate was diluted, in 0.5 $\log_{10}$ steps, with PBS containing 2% sarcosyl (weight/volume) and 4% BSA (weight/volume). The samples were then treated, at 37° C. for one hour, with proteinase K (PK; Roche) at a final concentration of 250 µg/ml. The digests were stopped by adding the proteinase inhibitors PMSF (=phenylmethylsulfonyl fluoride; Roche), Aprotinin (Sigma) and Leupeptin (Sigma), with the final concentration in each case being 20 µg/ml. Phosphotungstic acid was added to a final concentration of 0.3% and magnesium chloride was added to a final concentration of 2.72 mM. The samples were then incubated at 37° C. for 16 hours before being centrifuged at 14 000 rpm over a period of 30 minutes and at room temperature. The supernatants were removed and the pellets were resuspended in 50 µl of $H_2O$ which contained the proteinase inhibitors Leupeptin and Aprotinin in a quantity of 0.1 µg/ml. The samples were split and one half was denatured by adding 25 µl of 8M guanidinium hydrochloride (Gdn-HCl; Merck) and heating at 80° C. for a period of 5 minutes. After cooling down to room temperature, 950 µl of $H_2O$, containing the proteinase inhibitors Leupeptin and Aprotinin in a quantity of 0.1 µg/ml, were added. The untreated halves of the samples were diluted with 975 µl of $H_2O$ which contained the same proteinase inhibitors and 0.205 M Gdn-HCl. The diluted denatured and non-denatured (native) samples were transferred, in triplicate, to 96-well test plates (200 µl/well) whose wells had either been reactivated, at room temperature for 2 hours, with PBS containing 0.2% glutaraldehyde or were coated with the DSM ACC 2522, DSM ACC 2523 or DSM ACC 2524 monoclonal antibody which was diluted in PBS to a final concentration of 10 µg/ml. The samples were incubated, at room temperature for 2 hours, on the preactivated plates before the wells were washed with a solution of washing buffer (Wallac). The plates were then blocked, at room temperature for one hour, with TBS (TRIS-buffered saline) containing 5% BSA and then washed 3× with the washing buffer (Wallac) before being incubated, at room temperature for 2 hours and while agitating, with the reagent buffer (Wallac) containing the Europium-labeled monoclonal antibody 3F4. The plates were then washed 7× with the washing buffer before 200 µl of the enhancing solution (Wallac) were added/well. After agitating at room temperature for 10 minutes, the fluorescence originating from the Europium-bonded monoclonal antibody 3F4 was measured in a Discovery (Canberra Packard) fluorescence analyzer. The number of fluorescence signals which the analyzer measured in the denatured sample was then divided by the number of fluorescence signals which were obtained from the native samples. A denatured/native ratio which was higher than the ratio obtained for the PBS/BSA/sarcosyl dilution buffer indicated the presence of protease-resistant $PrP^{Sc}$ in the sample dilution(FIG. 1A). The sandwich CDI exhibits a 10- to 30-fold increase in sensitivity as compared with the conventional glutaraldehyde cross-linking method.

3. Improved Conformation-dependent Immunoassay Method without Treatment with Proteinase K Brain lysates containing human prions were added in small quantities to human plasma and diluted in human plasma in half-$\log_{10}$ steps. The dilutions were then treated as described in Example 2 except that no proteinase K was added (FIG. 2B). The sandwich configuration using the monoclonal antibodies derived from the cell line DSM ACC 2523 increases the sensitivity of the test 100- to 300-fold as compared with the glutaraldehyde cross-linking method.

4. Inhibition of Antibody Binding after Reduction of Prion Proteins

Purified $PrP^{Sc}$ which was isolated from the brain of a person who died of vCJD by the method described by Bolton (Bolton D C, 1987) was resuspended in phosphate-buffered saline containing 2% sarcosyl and 1% bovine serum albumin, sample was split, 1 ml aliquots were transferred to Eppendorf tubes and digested with proteinase K at a concentration of 65 µg/ml for one hour at 37° C. The reaction was stopped by adding protease inhibtors at concentrations known to persons skilled in the art and $PrP^{Sc}$ was precipitated by adding NaCl to a final concentration of 30% (weight/volume). The samples were incubated at 4° C. over night and then centrifuged at 16000×g for 30 min. The pellet was resuspended in 50 µl destilled water containing protease inhibitors at concentrations known to a person skilled in the art and then denatured at 4M guanidinium hydrochloride and heating for 6 minutes at 83° C. Three samples were treated identically in parallel except that $PrP^{Sc}$ was reduced in the presence of 3.3 mM dithiothreitol at the same time. One of these reduced samples was treated with 10 mM jodacetamide for 10 minutes to irreversibly methylate the thiol groups and prevent reoxidation. The second one of the reduced samples was oxidized by adding 0.2 mM oxidized glutathione for 2 hours at room temperature. The remaining samples were supplemented with buffer lacking glutathion and incubated for 2 hours at room temperature as well.

Figure 3:
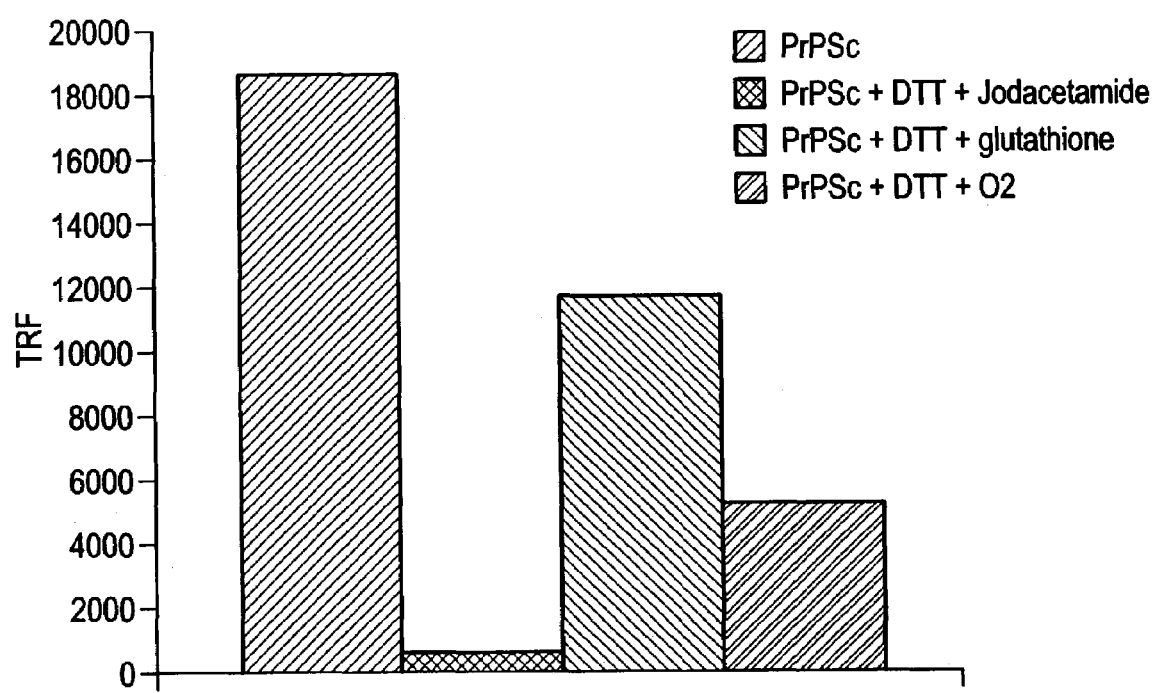

From each individual sample well 3×200 µl aliquots were then transferred to microtiter wells pretreated with glutaraldehyde as described in example 2 and incubated at room temperature for 2 hours while shaking. After blocking and washing of wells monoclonal antibodies DSM ACC 2522, DSM ACC 2523, or DSM ACC 2524 were added. After incubation for 1.5 hours at room temperature the antibody was removed by washing plates 7×. A secondary, antibody specific for murine immunoglobulines which was chemically conjugated with Europium chelate complexes was then added to the wells and incubated for 1.5 hours at room temperature while shaking. After removal of secondary antibody and washing the plates 7× the Europium was released from the bound secondary antibody using the enhance buffer provided by Wallac (Turku, Finland). The Europium fluorescence signal was then analyzed using a Discovery fluorescence analyzer (Canberra, Packard, Darmstadt, Germany). The non-reduced $PrP^{Sc}$ molecules produced a 30× higher signal than the reduced $PrP^{Sc}$ molecules (FIG. 3). This means that for efficient binding of antibodies DSM ACC 2522, DSM AC 2523, DSM ACC 2524 to human prion protein a disulfide bridge must exist. The binding to once reduced $PrP^{Sc}$ molecules can be reproduced by reconstructing the disulfide bridge. This is shown in FIG. 3: after oxidation of reduced $PrP^{Sc}$ molecules using oxidized glutathion or oxygen as oxidizing agents, the binding of Europium labeled antibody reached up to 60% of the signal obtained for the non-reduced samples.

FIGURES

FIG. 1: Binding of the antibodies according to the invention to human prion-protein. Homogenized brain of different species was separated in SDS-PAGE and transferred to nylon-membranes. Then a Western-Blot was performed using the monoclonal antibody 6H4 (Prionics, upper Figure) and in parallel the inventive antibody DSM ACC 2522 (lower Figure). Bound antibody was detected by an phosphatase coupled secondary antibody. Lane 1: molecular weight standard; lane 2: rat; lane 3: human; lane 4: African vervet monkey; lane 5: Syrian golden hamster; lane 6: bovine.

FIG. 2A: Comparison of the sandwich conformation-dependent immunoassay method and a conventional glutaraldehyde cross-linking method for detecting human prion protein with proteinase K, and using a monoclonal antibody according to the invention as the binding reagent. (See Example 2 for further details.)

FIG. 2B: Comparison of the sandwich conformation-dependent immunoassay method and a conventional glutaraldehyde cross-linking method for detecting human prion protein without proteinase K, and using a monoclonal antibody according to the invention as the binding reagent. (See Example 3 for further details.)

FIG. 3: Binding of the antibodies according to the invention to human prion-protein. Human, pathogenic prion-protein $PrP^{Sc}$, was denatured and before it was immobilized in a microtitratoin plate, it was either reduced by the addition of DTT and methylated with iodine acetamide. Or it was reduced by the addition of DTT and oxidized with glutathione, or it was reduced with DTT and oxidized with air ($O_2$). The immobilized prionproteins then were incubated with the inventive antibodies of cell-line DMS ACC 2523. Bound antibody was detected by an fluorescence labeled secondary antibody. TRF: time-resolved fluorescence. Reducing the disulfide-bridge in the prion-protein results in a loss of the fluorescence, which means the disappearance of the antibody binding.

REFERENCE LIST

Barry R A, et al. (1986). Monoclonal antibodies to the cellular and scrapie prion proteins. J Infect Dis 154, 518–521.

Bolton D C, et al. (1987). Isolation and structural studies of the intact scrapie agent protein. Arch Biochem Biophys 258, 579–590.

Harmeyer S, et al. (1998). Synthetic peptide vaccines yield monoclonal antibodies to cellular and pathological prion proteins of ruminants. J Gen Virol 79, 937–945.

Krasemann S, et al. (1999). Generation of monoclonal antibodies against prion proteins with an unconventional nucleic acid-based immunization strategy. J Biotechnol 73, 119–129.

Prusiner S B, et al. (1982). Further purification and characterization of scrapie prions. Biochemistry 21, 6942–6950.

Prusiner S B, et al. (1984). Purification and structural studies of a major scrapie prion protein. Cell 38, 127–134.

Prusiner S B. (1998). Prions. Proc Natl Acad Sci USA 95, 13363–13383.

Smales C M, et al. (2002). Protein modification during anti-viral heat-treatment bioprocessing of factor VIII concentrates, factor IX concentrates, and model proteins in the presence of sucrose. Biotechnol Bioeng 77, 37–48.

Zanusso G, et al. (1998). Prion protein expression in different species: analysis with a panel of new mAbs. Proc Natl Acad Sci USA 95, 8812–8816.

The invention claimed is:

1. An isolated antibody, which is formed by one of the hybridoma cell lines DSM ACC 2522, DSM ACC 2523 and DSM ACC 2524.

2. A method for detecting prions of human origin, which method comprises incubating an antibody as claimed in claim 1 with a sample comprising prions.

3. A conformation-dependent immunoassay method for detecting prions in a sample of human origin, which sample comprises prions which may adopt a first conformation and a second conformation, wherein the method comprises:
   a) adding an antibody to a first portion of the sample and determining the concentration of the first conformation, wherein the antibody is fixed to a solid support and wherein the antibody specifically detects prions of human origin and exhibits a higher affinity for the first conformation of the prions than for the second conformation;
   b) treating a second portion of the sample in order to increase the binding affinity of the second conformation of the prions for the antibody;
   c) adding the antibody to the treated second portion of the sample and determining the concentration of the second conformation; and
   d) comparing the concentrations of the first and second conformations in order to ascertain the presence of a pathogenic prion conformation;

wherein the antibody is formed by one of the hybridoma cell lines DSM ACC 2522, DSM ACC 2523 and DSM ACC 2524.

4. An immunoassay method as claimed in claim 3, wherein the sample is pretreated with a proteolytic enzyme.

5. An immunoassay method as claimed in claim 4, wherein the proteolytic enzyme is selected from proteinase K or dispase.

6. An immunoassay method as claimed in claim 3, further comprising exposing the sample to elevated temperature, elevated pressure or chemical reagents, which exposure converts at least 2% of prions in said sample into a form which binds to the antibody.

7. An immunoassay method as claimed in claim 3, wherein the quantity of the prions attached to the solid support via the antibody is measured by a second, labeled antibody.

8. An immunoassay method as claimed in claim 7, wherein the monoclonal antibody 3F4 is used as the second, labeled antibody.

9. An immunoassay method as claimed in claim 7, wherein the second, labeled antibody is labeled with a radioactive group, an enzymatic group or a fluorescent group.

10. An immunoassay method as claimed in claim 3, wherein the sample comprises prions of unknown origin.

11. A method as claimed in claim 3, wherein one of said first or second conformations is a $PrP^{Sc}$ conformation while the other is a $PrP^{C}$ conformation.

* * * * *